United States Patent
Tiep et al.

(10) Patent No.: US 9,468,732 B2
(45) Date of Patent: Oct. 18, 2016

(54) FLUIDIC-CONTROLLED RESERVOIR CANNULA

(71) Applicant: Inovo, Inc., Naples, FL (US)

(72) Inventors: Brian L. Tiep, Monrovia, CA (US); Rebecca E. Pacas, Monrovia, CA (US)

(73) Assignee: Inovo, Inc., Naples, FL (US)

( * ) Notice: Subject to any disclaimer, the term of this patent is extended or adjusted under 35 U.S.C. 154(b) by 268 days.

(21) Appl. No.: 13/956,290

(22) Filed: Jul. 31, 2013

(65) Prior Publication Data

US 2014/0130805 A1 May 15, 2014

Related U.S. Application Data

(60) Provisional application No. 61/678,091, filed on Jul. 31, 2012.

(51) Int. Cl.
*A61M 16/06* (2006.01)

(52) U.S. Cl.
CPC .. *A61M 16/0672* (2014.02); *A61M 2202/0208* (2013.01); *Y10T 29/49826* (2015.01)

(58) Field of Classification Search
CPC .. A61M 15/00; A61M 16/00; A61M 16/009; A61M 16/06; A61M 16/0666; A61M 16/0667; A61M 16/0683; A61M 16/20; A61M 16/0672; A61M 16/0677
USPC ........................................ 128/204.24, 207.18
See application file for complete search history.

(56) References Cited

U.S. PATENT DOCUMENTS

| | | | | |
|---|---|---|---|---|
| 4,422,456 A | * | 12/1983 | Tiep .................. | A61M 16/0666 128/207.17 |
| 7,328,703 B1 | * | 2/2008 | Tiep .................. | A61M 16/0666 128/204.24 |
| 8,001,968 B2 | * | 8/2011 | Doty .................. | A61M 16/009 128/204.18 |
| 2009/0320851 A1 | * | 12/2009 | Selvarajan ........ | A61M 16/0683 128/207.13 |

* cited by examiner

*Primary Examiner* — Lynne Anderson
*Assistant Examiner* — Peter S Vasat
(74) *Attorney, Agent, or Firm* — Bryan Cave LLP (57) ABSTRACT

A reservoir cannula is described that has a static fluidic control structure, in that it does not employ a membrane or other moving parts. Furthermore, the reservoir is open to ambient air instead of being sealed. In use, the reservoir cannula enables storage of oxygen and oxygen-rich gas in a storage chamber as well as in and around the patient's nasal passages and nasopharynx, which enables high volume oxygen delivery to the patient early in the next inhalation. Consequently, patients using this delivery mode can carry a smaller and lighter portable oxygen container for ambulatory oxygen, because lower flow oxygen is required to meet their oxygenation needs. In addition, patients requiring a higher flow of oxygen can achieve oxygenation levels previously achieved only by high flow mask or high flow nasal oxygen systems.

24 Claims, 9 Drawing Sheets

FLUIDIC-CONTROLLED RESERVOIR CANNULA

RELATED APPLICATION

This application claims the benefit of U.S. Provisional Application No. 61/678,091, which was filed on Jul. 31, 2012 and entitled FLUIDIC-CONTROLLED RESERVOIR CANNULA, the entire teachings of which are incorporated herein by reference.

BACKGROUND

Physicians often prescribe medical oxygen to certain patients such as those with chronic obstructive lung disease, restrictive lung disease, cystic fibrosis, bronchiectasis, or lung cancer. The medical oxygen is typically delivered to the patient via a supply tube called a nasal cannula, which is connected to a pressurized oxygen source. A gas regulator is typically employed to reduce the source pressure and meter the flow rate of the oxygen to the patient.

If the patient is bedridden in an institutional setting, such as a hospital or nursing home, the oxygen is frequently delivered to a wall port and supplied by a large bank of oxygen storage tanks. In such situations, the patient is often provided with a continuous flow of oxygen.

While oxygen delivery through a typical continuous flow nasal oxygen cannula is effective at oxygenating patients, it is wasteful. In particular, oxygen continues to be delivered during exhalation, which prevents the oxygen from reaching the patient's alveoli. In addition, oxygen delivered during late inhalation does not participate in alveolar gas exchange and therefore does not substantially oxygenate the patient.

The wasteful periods of oxygen delivery can be described with reference to the volume/time breathing cycle. The typical patient spends about ⅔ of the ventilatory cycle in exhalation. Oxygen delivered during that time will not flow toward the alveoli and therefore will be wasted.

During inhalation, about the last ⅓ of that volume fills the dead space (airways leading to the alveoli, but not into the alveoli). Because inhalation begins with a rapid upstroke but slows at the end, dead space inhalation occupies about the last ½ of the inhalation time. Oxygen delivered during this part of the ventilatory cycle is also substantially wasted.

All told, roughly the last ⅚ of oxygen delivery to the ventilatory time cycle is substantially wasted. Ideally, all of oxygen delivery should be targeted to the first ⅙ of the ventilatory cycle, which represents about the first ½ of the inhalation cycle. This is called "early inhalation", during which oxygen can flow into the alveoli and become available to the alveolar capillaries and to the blood circulation so that it can be delivered to the cells to support and enable metabolism.

Many patients are mobile and rely on oxygen stored in a portable oxygen cylinder. Because so much oxygen is wasted by continuous oxygen flow delivery, the limited supply of stored oxygen can be quickly depleted, especially for the smallest and most mobile cylinders, thus severely limiting the amount of time the patient can be active. Also, those patients require a higher flow setting due to the fact that patients who are exerting or exercising consume more energy and, consequently, more oxygen. To prolong the portable oxygen supply, numerous techniques have been devised to conserve the oxygen and optimize the oxygen delivery efficiency.

One technique to maximize oxygen delivery to the alveoli is to deliver oxygen through a transtracheal catheter through a surgical incision in the patient's neck. While this allows the oxygen to be delivered more directly to the alveoli, this technique is a surgical procedure that can be uncomfortable to the patient and introduces the risk of complications, including infections. Moreover, the transtracheal catheter requires a program of care.

Another technique employs pulse devices to deliver oxygen either periodically or on demand. The typical demand conserver senses the beginning of an inhalation and delivers a short pulse of oxygen in response. While the goal of the on-demand conservers is to optimize oxygen delivery, they vary in effectiveness. The conservers can be electronically or pneumatically controlled and often share a housing with the gas regulator.

Yet another technique employs a reservoir cannula. These devices typically use a membrane to form a sealed reservoir to store oxygen during exhalation for delivery during the next inhalation. Examples of typical reservoir cannula systems are described in U.S. Pat. No. 4,535,767 to Tiep et al., U.S. Pat. No. 4,572,177 to Tiep et al., and U.S. Pat. No. 7,328,703 to Tiep, the teachings of which are incorporated herein by reference in their entirety. Although these devices have been utilized for high flow delivery, the benefit of a storage chamber is defeated by the high flow (i.e. greater than 8 L/min) as the membrane is typically pushed to the open position and cannot cycle.

SUMMARY

A reservoir cannula in accordance with embodiments of the invention can include a static fluidic control structure, in that it does not employ a membrane or other moving parts. Furthermore, the reservoir can open to ambient air instead of being sealed. In use, the reservoir cannula can enable the storage of oxygen and oxygen-rich gas in a storage chamber as well as in and around the patient's nasal passages and nasopharynx, which can enable high volume oxygen delivery to the patient early in the next inhalation. Consequently, patients using certain embodiments of the invention can carry a smaller and lighter portable oxygen container for ambulatory oxygen, because lower flow oxygen may be required to meet their oxygenation needs. In addition, patients requiring a higher flow of oxygen may achieve oxygenation levels previously achieved only by high flow mask or high flow nasal oxygen systems.

In accordance with one embodiment of the invention, a gas reservoir cannula for controlling the delivery of oxygen to a patient can include an outer shell having an outer surface exposed to ambient air and inner surface defining a reservoir chamber and a static structure disposed within the reservoir chamber.

The outer shell can have a supply aperture and an exhaust aperture extending through the outer shell to the reservoir chamber.

The static structure can include a fluidic controller having a supply port, a nasal port, and a collection port. A supply tube can extend through the supply aperture in the outer shell and fitted to the supply port. A nasal prong can be fitted to the nasal port and extend through the exhaust aperture.

In addition, the exhaust aperture can have an open surface area dimension and the nasal prong can have an outer area dimension. The outer area dimension of the nasal prong can be less than that open surface area dimension of the exhaust aperture to permit gas to escape from the reservoir cannula. The escaped gas from the reservoir chamber can then be stored around the nasal prong.

In more specific embodiments, the nasal prong and the nasal port can include a cooperating alignment feature. Also, the outer shell can have a generally triangular cross section.

The fluidic controller can control delivery of gas from the reservoir chamber and the supply port in response to a human breathing cycle. More particularly, the collection port can be in communication with the reservoir chamber. Even more particularly, a collection tube having a proximal end can be fitted to the collection port and a distal end within the reservoir chamber. The collection port can thus enable oxygen to flow into and out of the reservoir chamber in response to a human breath cycle.

In accordance with one embodiment of the invention, a gas reservoir cannula for controlling the delivery of oxygen to a patient can include an outer shell having an outer surface exposed to ambient air and inner surface defining a reservoir chamber and a fluidic controller disposed within the reservoir chamber.

The outer shell can have a supply aperture and an exhaust aperture extending through the outer shell to the reservoir chamber. The exhaust aperture can be characterized by an open surface area dimension. More specifically, The outer shell can have a generally triangular cross section.

The fluidic controller can have a supply port and a nasal port. A supply tube can extend through the supply aperture in the outer shell and fitted to the supply port. A nasal prong characterized by an outer area dimension can be fitted to the nasal port and extend through the exhaust aperture. The outer area dimension of the nasal prong can be less than the open surface area dimension of the exhaust aperture to permit gas to escape from the reservoir cannula. That can allow the escaped gas to be stored around the nasal prong.

More particularly, the fluidic controller can be a static structure. Furthermore, the nasal prong and the nasal port can include a cooperating alignment feature. The fluidic controller can control delivery of gas from the reservoir chamber and the supply port in response to a human breathing cycle. The fluidic controller can further include a collection port in communication with the reservoir chamber, where a collection tube can have a proximal end fitted to the collection port and a distal end within the reservoir chamber. The collection port can thus enable oxygen to flow into and out of the reservoir chamber in response to a human breath cycle.

In accordance with yet another embodiment of the invention, a gas reservoir cannula for controlling the delivery of oxygen to a patient can include an outer shell having an outer surface exposed to ambient air and inner surface defining a reservoir chamber and a static structure disposed within the reservoir chamber.

The outer shell can have a pair of supply apertures and a pair of exhaust apertures extending through the outer shell to the reservoir chamber. The exhaust apertures can each have an open surface area dimension. More specifically, the outer shell can have a generally triangular cross section.

The static structure can include a fluidic controller having a pair of supply ports, a pair of nasal ports, and a pair of collection ports. More specifically, the fluidic controller can control delivery of gas from the reservoir chamber and the supply ports in response to a human breathing cycle.

A pair of supply tubes can extend through respective supply apertures in the outer shell and fitted to respective supply ports. A pair of nasal prongs, each having an outer area dimension, can be fitted to respective nasal ports and extend through respective exhaust apertures. The outer area dimension of the nasal prongs can be less than that open surface area dimensions of the respective exhaust aperture to permit gas to escape from the reservoir cannula. That can allow the escaped gas to be stored around the nasal prongs.

Embodiments of the invention also include methods of fabricating and using a gas reservoir cannula.

BRIEF DESCRIPTION OF THE DRAWINGS

The foregoing and other objects, features and advantages of the invention will be apparent from the following more particular description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Particular embodiments of the invention include a reservoir cannula that has a static fluidic control structure that it does not employ a membrane or other moving parts (i.e. dynamic structures). Furthermore, the reservoir is open to ambient air instead of being sealed. In use, the inventive reservoir cannula enables storage of oxygen and oxygen-rich gas in a storage chamber as well as in and around the patient's nasal passages and nasopharynx, which enables high volume oxygen delivery to the patient early in the next inhalation.

One benefit of a fluidic-controlled reservoir cannula according to particular embodiments of the invention is to improve upon the efficiency of oxygen delivery by a factor of about six relative to other oxygen delivery devices, such as standard nasal cannula, high flow oxygen delivery devices, and simple face masks. While continuous flow oxygen would ordinarily be wasted during exhalation, patients using the described delivery mode can carry a smaller and lighter portable oxygen container for ambulatory oxygen, because lower flow oxygen is required to meet their oxygenation needs. In addition, patients requiring a higher flow of oxygen can achieve oxygenation levels previously achieved only by high flow mask or high flow nasal oxygen systems (both of which are large and cumbersome).

Figure 1:
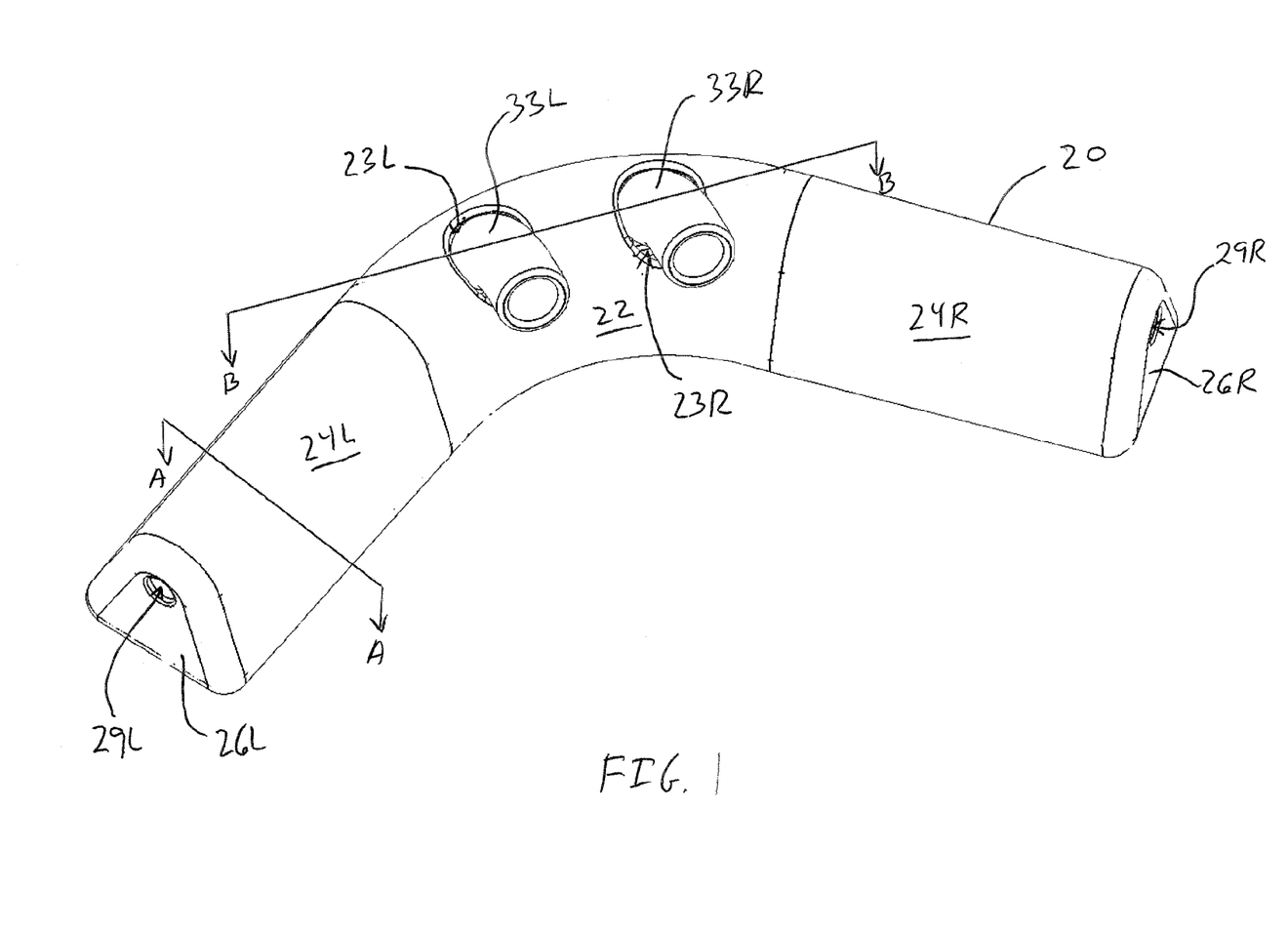
FIG. 1 is a perspective view of a reservoir cannula in accordance with an embodiment of the invention.

FIG. 1 is a perspective view of a reservoir cannula in accordance with an embodiment of the invention. As shown, the reservoir cannula includes an outer shell 20 having apertures to an interior reservoir chamber.

The apertures include supply apertures 29L, 29R through which respective supply tubing 70L, 70R (FIG. 2) from an oxygen supply source (possibly regulated by an oxygen regulator or pulse conserver) (not shown) extends. Also, the nasal prongs 33L, 33R extend from the reservoir chamber through respective nasal exhaust apertures 23L, 23R of the outer shell 20.

The nasal apertures 23L, 23R have a larger diameter than the outer diameter of the nasal prongs 33L, 33R suitable to provide low resistance for unencumbered exhaust to enrich the ambient air under the nostrils. In a particular embodiment, the nasal prongs 33L, 33R are circular and have a diameter of 0.280 in (open area dimension of about 0.062 in$^2$) and the nasal apertures 23L, 23R are circular and have an outer diameter of 0.315 in (outer area dimension of about 0.078 in$^2$). The additional 0.016 in$^2$ of the nasal apertures 23L, 23R at the base of nasal prongs 33L, 33R provides suitable pressure relief and delivery of oxygen stored in the reservoir chamber. Because the nasal apertures 23L, 23R have a larger diameter than the outer diameter of the nasal prongs 33L, 33R, the reservoir within the outer shell 20 is open to the ambient environment, as opposed to prior art sealed reservoirs, allowing some gas to escape through the nasal apertures 23L, 23R.

The outer shell 20 can be fabricated using any suitable technique, including injection molding and extruding. Because the reservoir cannula is intended to be worn for extended periods of time, the outer shell 20 should be soft, flexible, compliant, and comfortable to wear. To those ends, the outer shell can be fabricated from medical grade Polyvinyl Chloride (PVC) or other suitable materials. In a particular embodiment, the outer shell 20 comprises a plurality of distinct overlapping sections, which are adhered together to form an integral structure. As shown, the outer shell 20 includes a center or core segment 22, a pair of lateral segments 24L, 24R, and end caps 26L, 26R that can be shaped into a single piece. However, the outer shell 20 can be formed from a single piece or more segments than shown. The outer shell 20 can be translucent, transparent, opaque, or a combination. The outer shell 20 can also be colored if desired.

As shown, the outer shell segments have a cross section when sectioned in the transverse plane along lines A-A that is generally shaped as an equilateral triangular with radiused apexes. One face of the outer shell fits against the patient's face under the nose. Because the reservoir cannula is worn below the nose of a patient, the core segment 22 is curved to fit over the upper lip of a patient so that the outer shell 20 generally follows the contour of a human face. By utilizing the triangular geometry, the resulting reservoir has a larger volume (about 20 ml) than commercially-available undernose reservoir cannulas, while appearing physically smaller on the face.

More details of the reservoir cannula, including specific dimensions and components are provided in the incorporated U.S. Provisional Application. It should be understood that other dimensions can be employed that may provide suitable performance.

Figure 2:
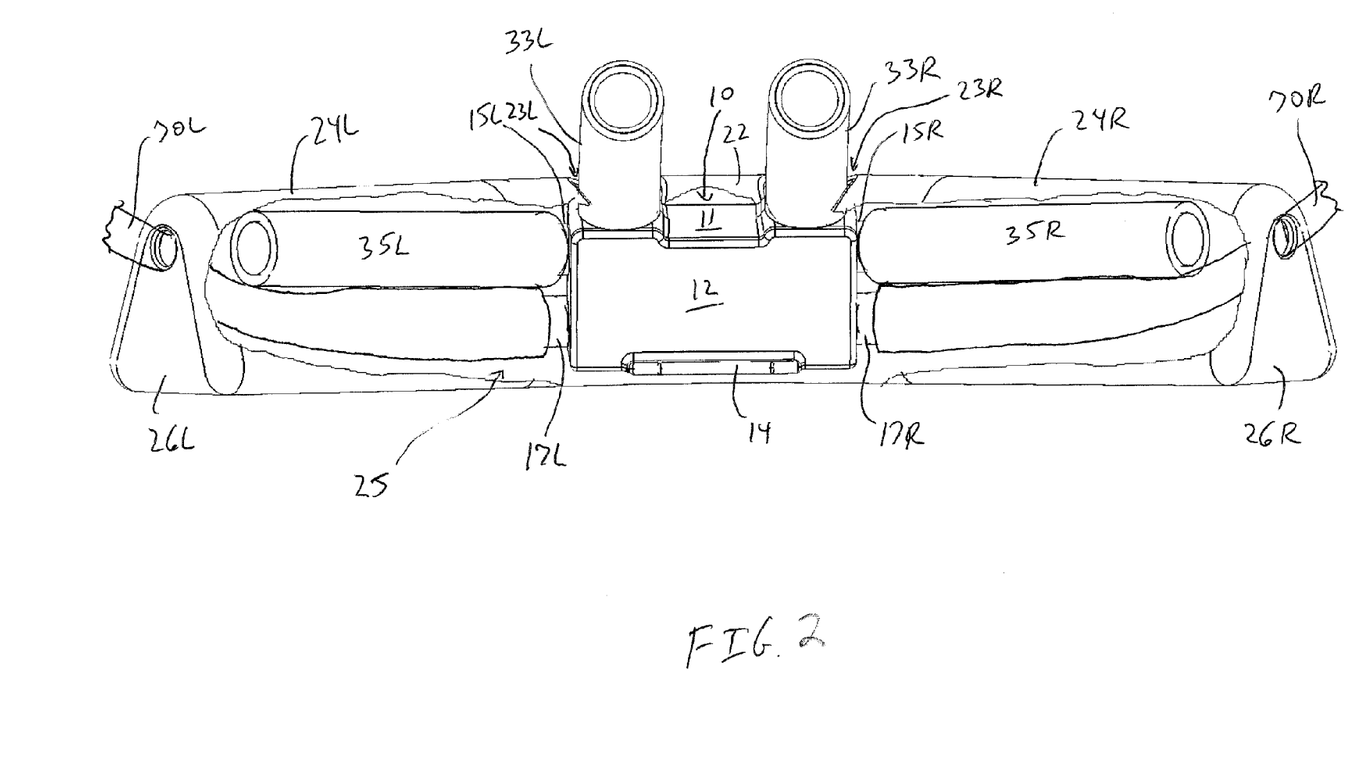
FIG. 2 is a front view of the reservoir cannula of FIG. 1 with a portion of the outer shell cut away to show internal parts.

FIG. 2 is a front view of the reservoir cannula of FIG. 1 with a portion of the outer shell cut away to show internal parts. As shown, a fluidic controller (or distributor) module assembly 10 (described below in more detail) is disposed within the outer shell 20, which defines a reservoir chamber 25. As shown, the fluidic controller 10 includes laterally extending collection ports 15L, 15R and supply ports 17L, 17R. Collection tubes 35L, 35R are shown coupled to respective collection ports 15L, 15R at their proximal ends and open to the reservoir chamber 25 at their distal ends. The collection tubes are flexible to facilitate flexing of the reservoir cannula when fitted on a patient. In a particular embodiment, the collection tubes 35L, 35R are fabricated from medical grade PVC.

In use, respective supply tubing 70L, 70R from the oxygen supply source (not shown) extends through supply apertures 29L, 29R and connects with the supply ports 17L, 17R. In a particular embodiment, the supply tubing 70L, 70R can be shaped to fit over the patent's ears and help hold the device in position. Thus, the device can be secured under a patient's nose by the lateral supply tubing 70L, 70R exiting the outer shell 20 through respective supply apertures 29L, 29R and extending to the back of the head over the ears and drawn together with a bolla or Y-type tube connector.

The nasal prongs 33L, 33R extend from the fluidic controller 10 and through respective nasal apertures 23L, 23R of the outer shell 20. In a particular embodiment, the nasal tubes 33L, 33R are formed from medical grade PVC.

In a particular embodiment, the fluidic controller assembly 10 is a plastic structure. While the outer shell 20 is generally soft for comfortable wear, the fluidic controller assembly 10 should be rigid to maintain the geometric configuration for effective fluidic operation. In a particular embodiment, the working component 11 and the plate component 12 of the fluidic controller assembly are fabricated from TOYOLAC® ABS resin, which is a thermoplastic material comprising acrylonitrile, butadiene and styrene and commercially available from Toray Industries, Inc (Toray Resin Company, Troy, Mich.). Other suitable materials can be used to fabricate the fluidic controller assembly 10 by any suitable method, including injection molding, machining, and 3-D printing.

Note that the fluidic controller assembly 10 includes a curved bridge structure 14 to help support the reservoir cannula above the wearer's lip.

Figure 3:
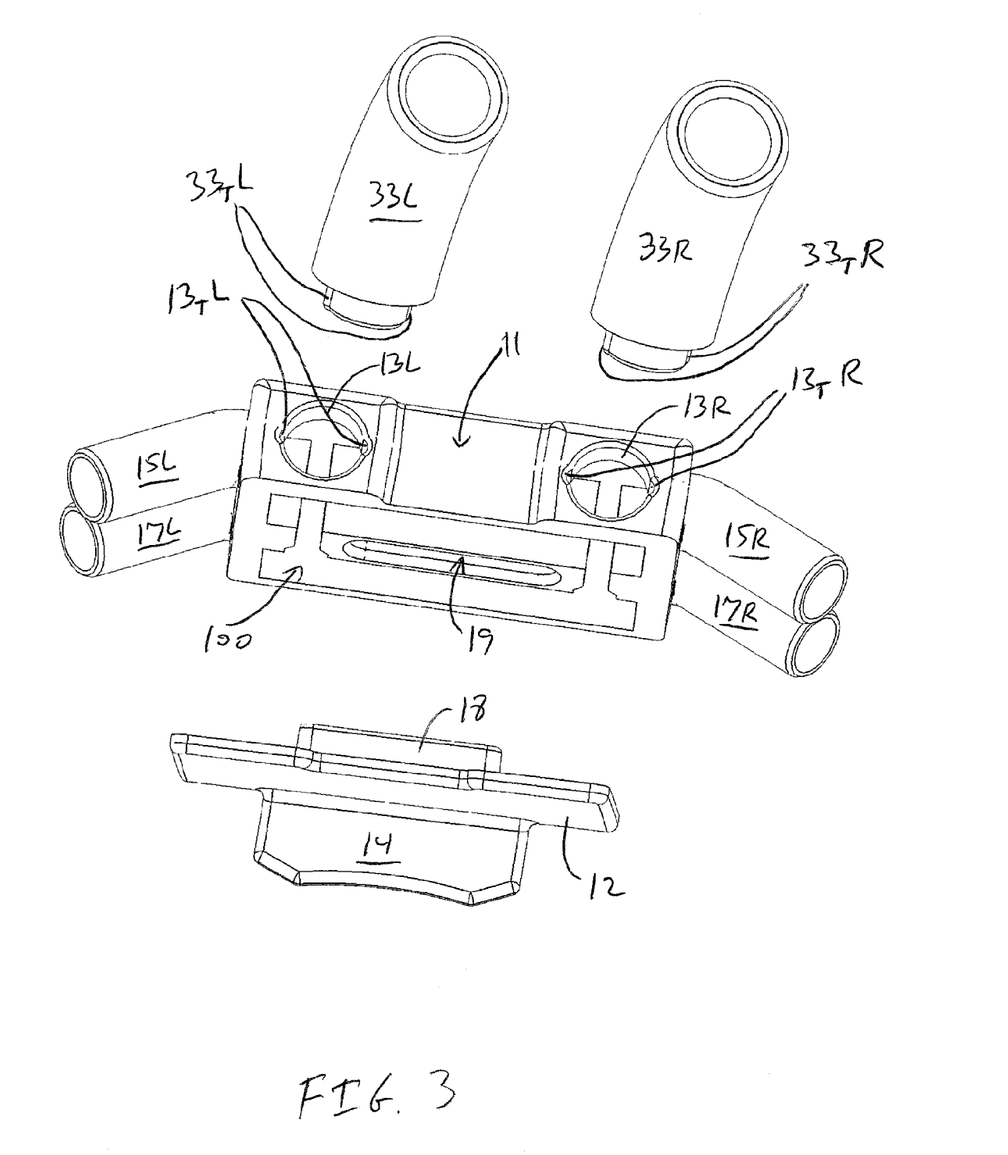
FIG. 3 is an exploded perspective view of the fluidic control module of FIG. 2.

FIG. 3 is an exploded perspective view of the fluidic control module of FIG. 2. Shown are the working component 11, rear plate component 12, and nasal prongs 33L, 33R.

The working component 11 houses a fluidic cavity 100 in gaseous communication with a plurality of ports. The ports include the nasal ports 13L, 13R, collection ports 15L, 15R, and the supply ports 17L, 17R. The nasal prongs 33L, 33R attach to the respective nasal ports 13L, 13R via cooperating alignment features, such as port notch 13$_T$L, 13$_T$R and prong tabs, 33$_T$L, 33$_T$R,. Also shown is an assembly slot 19.

The plate component 12 includes the curved bridge structure 14 and an assembly projection 18, which fits within the assembly slot 19 of FIG. 3.

While shown as being generally cylindrical, the nasal tubes 33L, 33R can be fluted or have another geometry to compliment its use in the nose.

Figure 4:
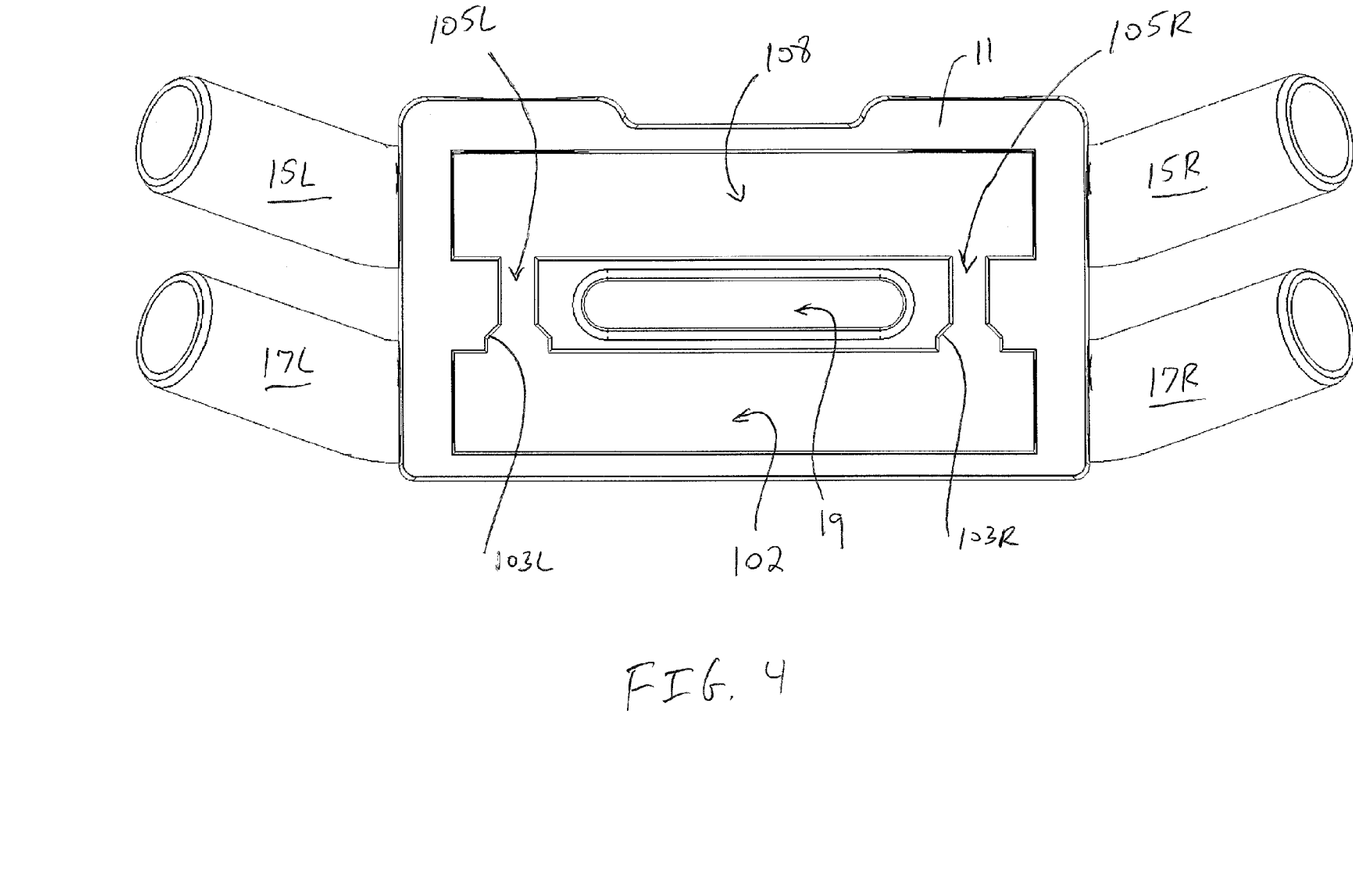
FIG. 4 is a planar view of a particular working component of the fluidic controller of FIG. 3.

FIG. 4 is a planar view of a particular working component of the fluidic controller of FIG. 3. As shown, the fluidic cavity 100 includes an input cavity 102 and an exchange cavity 108, which are interconnected by delivery jet channels 105L, 105R. The input cavity 102 is coupled to the supply ports 17L, 17R and the delivery jet channels 105L, 105R. The delivery jet channels 105L, 105R have counterbores 103L, 103R at the interface with the input cavity 102 to reduce turbulence and facilitate a smooth flow of gas into the delivery jets 105L, 105R. The exchange cavity 108 is coupled to the nasal ports 13L, 13R (see FIG. 3), the lateral channel ports 15L, 15R, and the delivery jet channels 105L, 105R.

The combination of features yields enhanced oxygen delivery to the patient in response to an inhalation and enhanced oxygen storage in response to an exhalation or accumulation when the patient is between breaths. A particular embodiment of the invention does not require control adjustments due to the driving pressure and geometry. The device can operate efficiently with gas pressures up to at least 60 mmHg.

It should be understood that the fluidic cavity 100 is designed and fabricated to operate in response to the patient's breathing. That functioning will now be described.

Figure 5:
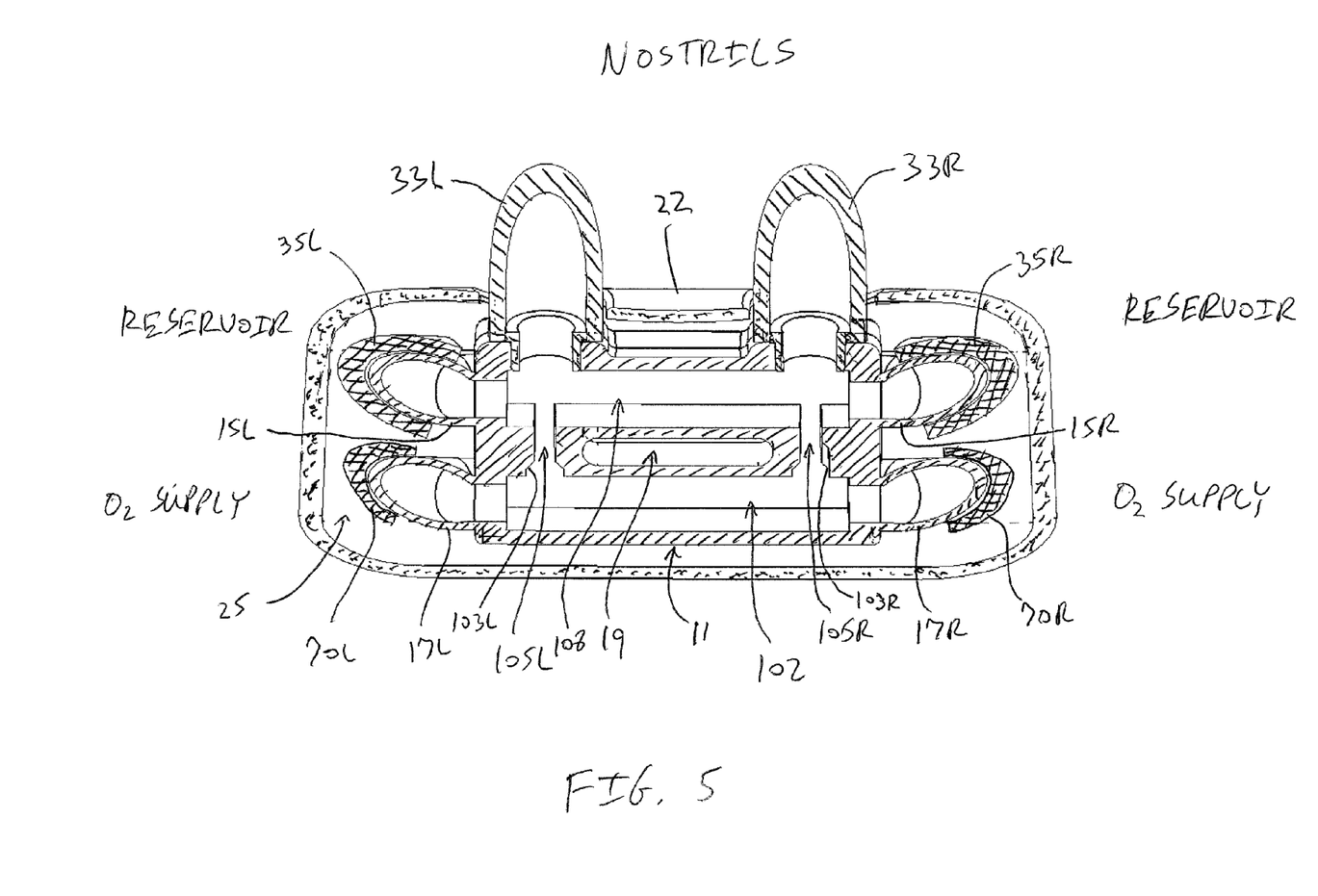
FIG. 5 is a cross-section of the reservoir cannula taken along line B-B of FIG. 1.

FIG. 5 is a cross-section of the reservoir cannula taken along line B-B of FIG. 1. This view sections the working component 11 of the fluidic controller showing the internal cavities of FIG. 4. Shown more clearly are the connection of the nasal prongs 33L, 33R to the working component 11, the fitting of the collection tubes 35L, 35R to the collection ports 15L, 15R, and the fitting of the supply tubes 70L, 70R to the supply ports 17L, 17R. As shown, the nasal prongs 33L, 33R communicate with a patient's nostrils, the collection tubes 35L, 35R communicate with the reservoir chamber 25, and the supply tubes 70L, 70R communicate with a source of compressed medical oxygen.

This figure will now be utilized to illustrate operation of the fluidic controller during a breathing cycle. It has been found that the fluidic controller functions well over a wide range of oxygen flow rates, in particular, from at least 0.5 L/min to 20 L/min.

Figure 6:
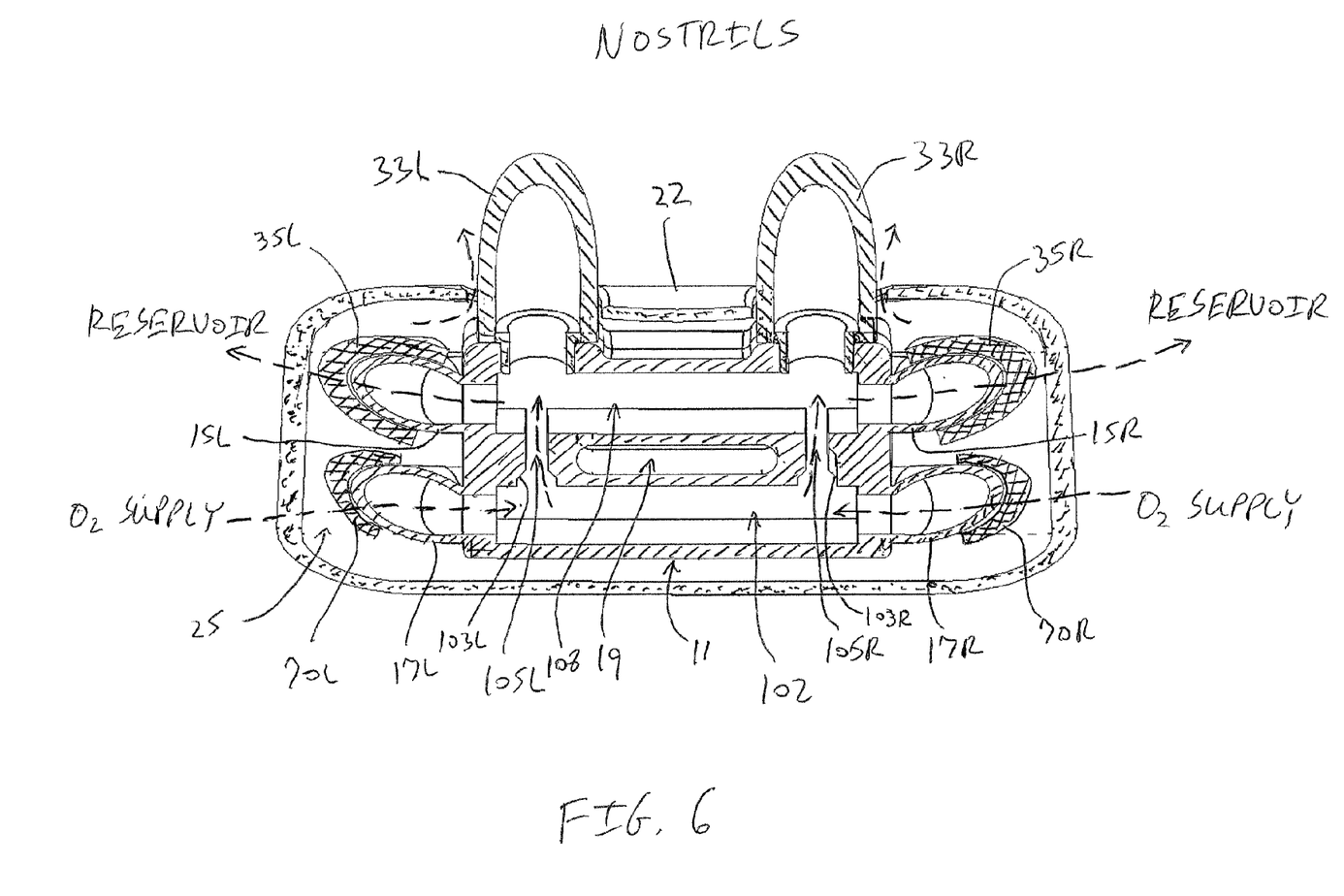
FIG. 6 is a cross-section of the reservoir cannula taken along line B-B of FIG. 1 showing gas flow during a dwell period in a breathing cycle.

FIG. 6 is a cross-section of the reservoir cannula taken along line B-B of FIG. 1 showing gas flow during a dwell period in a breathing cycle. During a dwell period, a person is neither inhaling nor exhaling.

In use, compressed gas (pressurized oxygen) enters the fluidic module 10 (FIG. 1) through supply ports 17L, 17R and into the lower input chamber 102. The pressurized oxygen is forced through jet channels 105L, 105R, creating a rapid moving jet of oxygen into the upper exchange chambers 108.

During use, the input cavity 102 is pressurized to the pressure supplied by the regulator (e.g. 20 or 50 psi). Oxygen then flows through the delivery jets 105L, 105R at an increased velocity as determined by the minimum orifice cross-sectional area of the jets 105L, 105R, which in a particular embodiment is about 0.002 in$^2$.

During a dwell period, a backpressure exists in the nares. That backpressure extends to the exchange chamber 108 and causes the oxygen to flow laterally into the reservoir chamber 25 through the lateral channel ports 15L, 15R to promote storage. Oxygen will thus be stored in the collection tubes 35L, 35R, the reservoir chamber 25, and, ultimately, outside the outer shell 20 in the area of the nasal apertures 23L, 23R. Further details will now be described.

Figure 7:
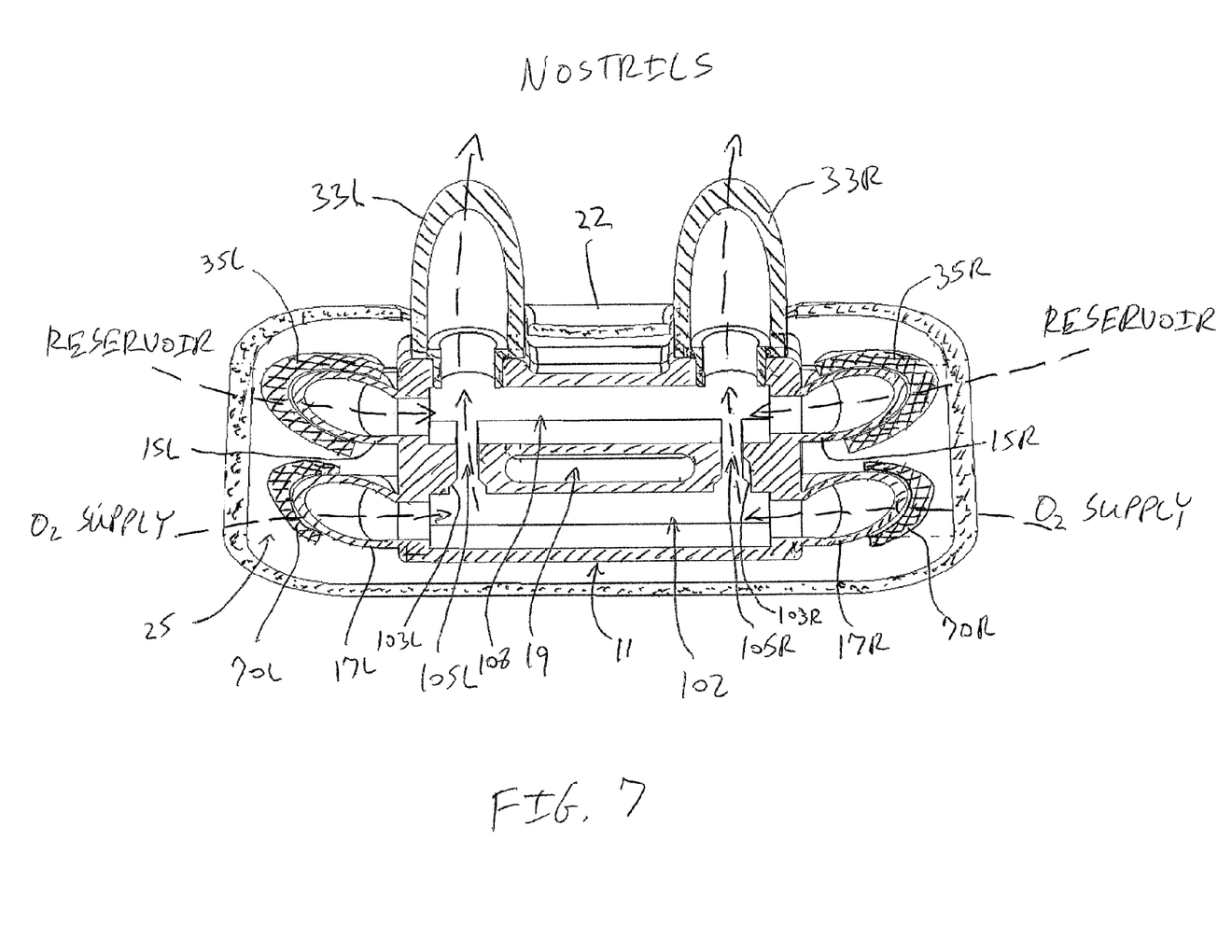
FIG. 7 is a cross-section of the reservoir cannula taken along line B-B of FIG. 1 showing gas flow during an inhalation breath.

FIG. 7 is a cross-section of the reservoir cannula taken along line B-B of FIG. 1 showing gas flow during an inhalation breath. The particular geometry of the fluidic controller biases oxygen flow toward the patient.

When the patient inhales through the nose, the oxygen jet flows unencumbered through the nasal prongs 33L, 33R and into the patient's nares. In that process, the rapid flow of oxygen through the exchange chamber 108 creates a negative pressure. In response to the pressure drop, oxygen from the input cavity 102 flows through the delivery jets 105L, 105R and through the nasal prongs 33L, 33R. In effect, a Venturi effect is created that also draws gas stored in the collection tubes 35L, 35R and the reservoir chamber 25 into the exchange cavity 108. Furthermore, any oxygen-rich gas accumulated under the nose will also be drawn directly into the patient's nasal cavity. It should be understood, that the accumulated oxygen-rich gas outside of the outer shell is also near the mouth so that mouth breathing can also benefit. As a result, the patient receives the stored oxygen in addition to the flow of oxygen from the oxygen supply.

As such, the inhalation breath draws gas from the collection tubes 35L, 35R, the reservoir chamber 25, and around the nasal apertures 23L, 23R. Thus, the medical oxygen from the supply source is supplemented by the stored oxygen and oxygen-rich gas—all of which occur early in the inhalation period to increase oxygen delivery to the alveoli. Furthermore, that stored exhaled gas may include warm and moist exhaled gas, which moderates the oxygen flow to provide the patient with an oxygen-rich gas mixture that is gentler on the patient's nasal passages than the more typical fresh oxygen flow.

Figure 8:
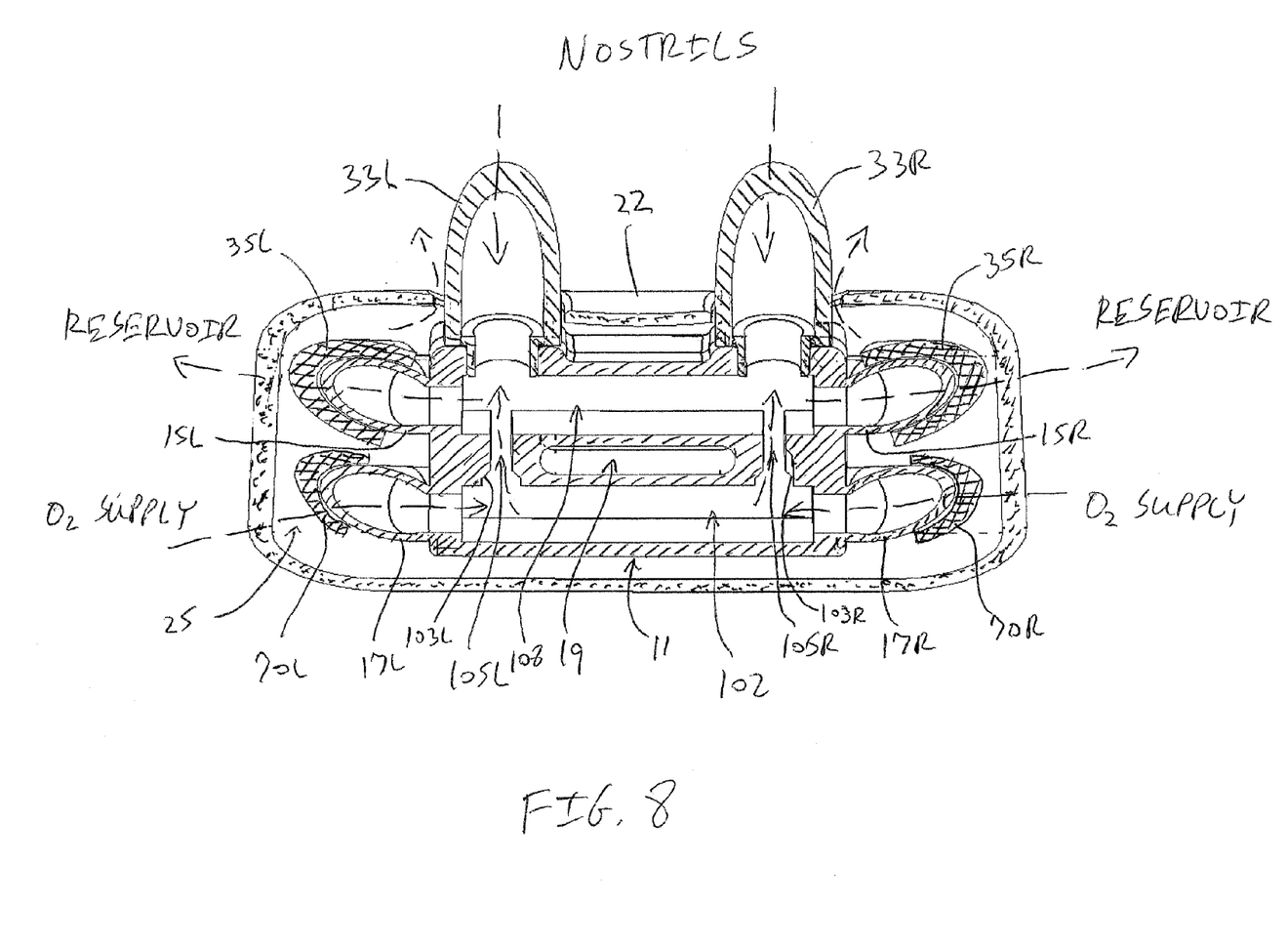
FIG. 8 is a cross-section of the reservoir cannula taken along line B-B of FIG. 1 showing gas flow during an exhalation breath.

FIG. 8 is a cross-section of the reservoir cannula taken along line B-B of FIG. 1 showing gas flow during an exhalation breath. When the patient exhales through the nose a back pressure is created, the patient forces gas through the nasal prongs 33L, 33R, which increases the pressure in the exchange cavity 108. Again, the exhaled gas is from the patient's upper respiratory tract and is oxygen rich. That oxygen-rich gas can flows into the collection tubes 35L, 35R under low flow conditions. Under high flow rates, the oxygen flow from the jets 105L, 105R overcomes the flow of exhaled gas and the reservoir chamber 25 fills with the supplied oxygen. At lower flow rates, the exhaled gas, which is mostly oxygen, can mix in the reservoir chamber 25 with the fresh oxygen. Such mixing humidifies and helps warm the stored gas, which is particularly noticeable at lower flow rates (e.g., below about 4 L/min).

The gas then flows out of the collection tubes 35L, 35R and into the far ends of the reservoir chamber 25 bounded by the outer shell 20. As can be appreciated, the collection tubes 35L, 35R extend well into the reservoir chamber 25 to encourage gas flow to backfill the reservoir chamber 25.

In addition, some of the oxygen-rich gas can escape from the reservoir chamber 25 through the nasal apertures 23L, 23R, which act as a pressure relief. That vented oxygen-rich gas collects under the patient's nose around the nasal prongs 33L, 33R. As should be understood, the next inhalation breath will draw that oxygen-rich gas back into the patient through both the nasal tubes 33L, 33R and from the area under the nose (i.e. oxygen-rich gas that has escaped through the nasal apertures 23L, 23R). In addition, storage also occurs in the nasal passages and nasopharynx when oxygen is delivering at high flows, in particular beyond about 8 L/min.

Particular embodiments of the fluidic-controlled reservoir cannula provide significant advantages over prior solutions, namely:

More efficient and effective oxygen delivery.
 Oxygen storage in the reservoir occurs under both low flow delivery and high flow delivery.
 Works with pursed lips breathing because it does not require the patient to exhale through the nasal passages and into module in order to reset a membrane. This aspect is particularly advantageous under low flow conditions.
 Embodiment is smaller and less obtrusive, because there is no membrane.
 It is more comfortable and allows patients to eat with the device in place.

Embodiment is more reliable because the device has no membrane or moving parts.

Works ideally with both low flow portable oxygen therapy and high flow for patients with high flow requirements.

The device has been found to achieve adequate oxygenation at 10 L/min that is equivalent to nasal body temperature and humidity oxygen up to about 40 L/min of 80% concentration.

The geometry of the fluidic module, in particular the jets and gas flow interactions, promotes efficient storage and retrieval of oxygen.

Figure 9:
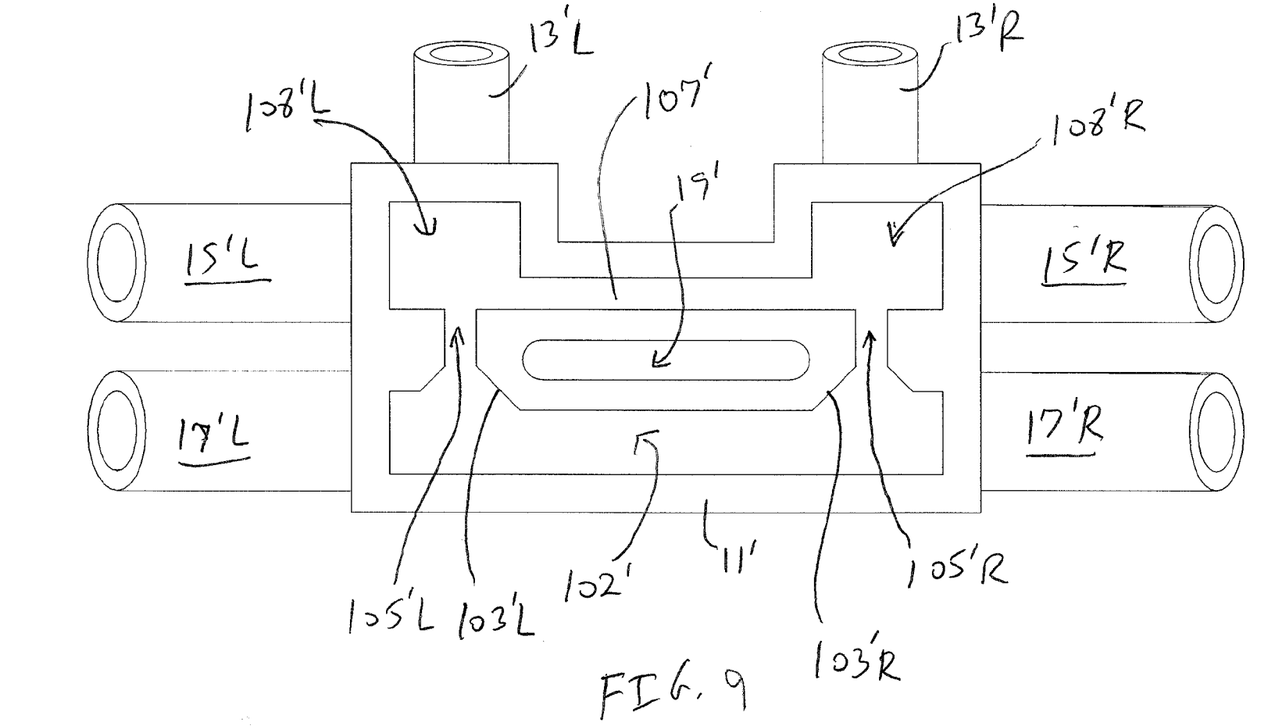
FIG. 9 is a planar view of another embodiment of a working component for a fluidic controller.

FIG. 9 is a planar view of another embodiment of a working component of a fluidic controller of FIG. 3. As shown, a fluidic cavity includes an input cavity 102' and an exchange cavity 108', which are interconnected by delivery jets 105L', 105R'. The input cavity 102' is coupled to cannula ports 17L', 17R' and the delivery jets 105L', 105R'. The delivery jet channels 105'L, 105'R have counter-bores 103'L, 103'R at the interface with the input cavity 102' to reduce turbulence and facilitate a smooth flow of gas into the delivery jets 105'L, 105'R. As shown, the exchange cavity includes a pair of interconnected port chambers 108'L, 108'R interconnected by a passageway 107', each port chamber 108'L, 108'R is coupled to a respective nasal port 13'L, 13'R, lateral channel port 15'L, 15'R, and delivery jet 105'L, 105'R. Note that the nasal ports 13'L, 13'R can be integrally formed with and extend from the working component 11' for receiving pliable nasal prong tubing (not shown). A fluidic controller employing this geometry can operate and perform similar to the embodiment shown in FIG. 4, but can be more difficult to assemble within the outer shell due to the extending nasal ports 13'L, 13'R.

While the particular fluidic controllers shown and described above are compact and can be assembled within the outer shell, it should be understood that other arrangements of the fluidic controller can be employed in a working reservoir cannula. In particular, the fluidic controller assembly can be modified from the above-described embodiments. For example, an embodiment can have more or fewer ports than shown. Specifically, the fluidic controller assembly can have a single supply port to receive oxygen from the oxygen source. In other embodiments, the working component of the fluidic controller can be integrated to the inner surface of the outer shell core segment. In such an embodiment, the outer shell can form the back plate to seal the fluidic chambers and the bridge structure and can be formed on the core segment. In another embodiment, the fluidic controller can be formed on the outer surface of the outer shell.

While this invention has been particularly shown and described with references to particular embodiments, it will be understood by those skilled in the art that various changes in form and details may be made to the embodiments without departing from the scope of the invention encompassed by the appended claims. For example, various features of the embodiments described and shown can be omitted or combined with each other.

What is claimed is:

1. A gas reservoir cannula for controlling the delivery of oxygen to a patient, comprising:
    an outer shell having an outer surface exposed to ambient air and inner surface defining a reservoir chamber, wherein a supply aperture and an exhaust aperture extend through the outer shell to the reservoir chamber, the exhaust aperture having an open surface area dimension;
    a static structure disposed within the reservoir chamber, the static structure including a fluidic controller having a supply port, a nasal port, and a collection port;
    a supply tube extending through the supply aperture in the outer shell and fitted to the supply port; and
    a nasal prong having an outer area dimension fitted to the nasal port and extending through the exhaust aperture, wherein the outer area dimension of the nasal prong is less than the open surface area dimension of the exhaust aperture to permit pas to escape from the reservoir cannula.

2. The gas reservoir cannula of claim 1 wherein escaped gas from the reservoir chamber is stored around the nasal prong.

3. The gas reservoir cannula of claim 1 wherein the nasal prong and the nasal port include a cooperating alignment feature.

4. The gas reservoir cannula of claim 1 wherein the fluidic controller controls delivery of gas from the reservoir chamber and the supply port in response to a human breathing cycle.

5. The gas reservoir cannula of claim 1 wherein the collection port is in communication with the reservoir chamber.

6. The gas reservoir cannula of claim 5 further comprising a collection tube having a proximal end fitted to the collection port and a distal end within the reservoir chamber.

7. The gas reservoir cannula of claim 6 wherein the collection port enables oxygen to flow into and out of the reservoir chamber in response to a human breath cycle.

8. The gas reservoir cannula of claim 1 wherein the outer shell has a generally triangular cross section.

9. A gas reservoir cannula for controlling the delivery of oxygen to a patient, comprising:
    an outer shell having an outer surface exposed to ambient air and inner surface defining a reservoir chamber, wherein a supply aperture and an exhaust aperture extend through the outer shell to the reservoir chamber, the exhaust aperture having an open surface area dimension;
    a fluidic controller disposed within the reservoir chamber, the fluidic controller having a supply port and a nasal port;
    a supply tube extending through the supply aperture in the outer shell and fitted to the supply port; and
    a nasal prong having an outer area dimension fitted to the nasal port and extending through the exhaust aperture, wherein the outer area dimension of the nasal prong is less than the open surface area dimension of the exhaust aperture to permit gas to escape from the reservoir cannula.

10. The gas reservoir cannula of claim 9 wherein escaped gas from the reservoir chamber is stored around the nasal prong.

11. The gas reservoir cannula of claim 9 wherein the fluidic controller is a static structure.

12. The gas reservoir cannula of claim 11 wherein the nasal prong and the nasal port include a cooperating alignment feature.

13. The gas reservoir cannula of claim 11 wherein the fluidic controller controls delivery of gas from the reservoir chamber and the supply port in response to a human breathing cycle.

14. The gas reservoir cannula of claim 11 wherein the fluidic controller further comprises a collection port in communication with the reservoir chamber.

15. The gas reservoir cannula of claim 14 further comprising a collection tube having a proximal end fitted to the collection port and a distal end within the reservoir chamber.

16. The gas reservoir cannula of claim 15 wherein the collection port enables oxygen to flow into and out of the reservoir chamber in response to a human breath cycle.

17. The gas reservoir cannula of claim 9 wherein the outer shell has a generally triangular cross section.

18. A gas reservoir cannula for controlling the delivery of oxygen to a patient, comprising:
an outer shell having an outer surface exposed to ambient air and inner surface defining a reservoir chamber, wherein a pair of supply apertures and a pair of exhaust apertures extend through the outer shell to the reservoir chamber, the exhaust apertures each having an open surface area dimension;
a static structure disposed within the reservoir chamber, the static structure including a fluidic controller having a pair of supply ports, a pair of nasal ports, and at least one collection port;
a pair of supply tubes, each extending through a respective supply aperture in the outer shell and fitted to a respective supply port; and
a pair of nasal prongs, each having an outer area dimension and fitted to a respective nasal port and extending through a respective exhaust aperture, wherein the outer area dimension of the nasal prongs is less than the open surface area dimensions of the respective exhaust aperture to permit gas to escape from the reservoir cannula.

19. The gas reservoir cannula of claim 18 wherein escaped gas from the reservoir chamber is stored around the nasal prongs.

20. The gas reservoir cannula of claim 18 wherein the fluidic controller controls delivery of gas from the reservoir chamber and the supply ports in response to a human breathing cycle.

21. The gas reservoir cannula of claim 18 wherein the outer shell has a generally triangular cross section.

22. A method of fabricating a gas reservoir cannula for controlling the delivery of oxygen to a patient, comprising:
fabricating a static structure including a fluidic controller having a supply port, a nasal port, and a collection port;
fabricating an outer shell having an outer surface exposed to ambient air and inner surface defining a reservoir chamber;
forming a supply aperture and an exhaust aperture through the outer shell to the reservoir chamber, the exhaust aperture having an open surface area dimension;
extending a supply tube through the supply aperture in the outer shell;
disposing the static structure within the reservoir chamber;
fitting the supply tube to the supply port; and
fitting a nasal prong having an outer area dimension to the nasal port to extend through the exhaust aperture, wherein the outer area dimension of the nasal prong is less than the open surface area dimension of the exhaust aperture to permit gas to escape from the reservoir cannula.

23. A method of fabricating a gas reservoir cannula for controlling the delivery of oxygen to a patient, comprising:
fabricating a fluidic controller having a supply port and a nasal port;
fabricating an outer shell having an outer surface exposed to ambient air and inner surface defining a reservoir chamber;
forming a supply aperture and an exhaust aperture through the outer shell to the reservoir chamber, the exhaust aperture having an open surface area dimension;
extending a supply tube through the supply aperture in the outer shell;
disposing the fluidic controller within the reservoir chamber;
fitting the supply tube to the supply port; and
fitting a nasal prong having an outer area dimension to the nasal port to extend through the exhaust aperture, the outer area dimension of the nasal prong being less than the open surface area dimension of the exhaust aperture.

24. A method of fabricating a gas reservoir cannula for controlling the delivery of oxygen to a patient, comprising:
fabricating a static structure including a fluidic controller having a pair of supply ports, a pair of nasal ports, and a pair of collection ports;
fabricating an outer shell having an outer surface exposed to ambient air and inner surface defining a reservoir chamber;
forming a pair of supply apertures and a pair of exhaust apertures through the outer shell to the reservoir chamber, the exhaust apertures each having an open surface area dimension;
extending a pair of supply tubes through respective supply apertures in the outer shell;
disposing the static structure within the reservoir chamber;
fitting the supply tubes to respective supply ports; and
fitting a pair of nasal prongs, each having an outer area dimension, to respective nasal ports to extend through the exhaust aperture, the outer area dimension of each nasal prong being less than the open surface area dimension of the respective exhaust aperture.

* * * * *